United States Patent [19]

Weeks et al.

[11] Patent Number: 4,802,885
[45] Date of Patent: Feb. 7, 1989

[54] SELF SEALING SUBCUTANEOUS INFUSION AND WITHDRAWAL DEVICE

[75] Inventors: Vaughan B. Weeks; Jeffrey E. Bark, both of Racine, Wis.

[73] Assignee: Medical Engineering Corporation, Racine, Wis.

[21] Appl. No.: 875,421

[22] Filed: Jun. 17, 1986

[51] Int. Cl.$^4$ ............................................. A61M 11/00
[52] U.S. Cl. ...................................... 604/93; 604/132; 604/175
[58] Field of Search ............... 604/891, 870, 116, 112, 604/132, 175, 183–185, 905, 93, 415, 201, 86, 88, 148; 128/DIG. 5, 7 R

[56] References Cited

U.S. PATENT DOCUMENTS

| | | | |
|---|---|---|---|
| 4,193,397 | 3/1980 | Tucker et al. | 604/49 X |
| 4,400,169 | 8/1983 | Stephen | 604/49 |
| 4,543,088 | 9/1988 | Bootman et al. | 604/93 |
| 4,626,244 | 12/1986 | Reinicke | 604/141 |
| 4,655,765 | 4/1987 | Swift | 604/891 |

Primary Examiner—John D. Yasko
Attorney, Agent, or Firm—Stuart E. Krieger

[57] ABSTRACT

The self-sealing subcutaneous infusion and withdrawal device or septum includes a cup-shaped needle stop member that defines a fluid chamber having a fluid transfer opening. A jacket envelops the needle stop member and includes an integrally formed delivery tube that aligns with the fluid transfer opening in the needle stop member. The fluid chamber of the needle stop member is sealed by a needle penetrable sealing member that is forced against a wall of the needle stop member by a clamping member to provide a mechanical leak-tight seal. The seal member has opposite convex surfaces which cooperate with the clamping member to impose a compression force upon a needle that penetrates the seal member during the fluid infusion and fluid withdrawal processes.

18 Claims, 3 Drawing Sheets

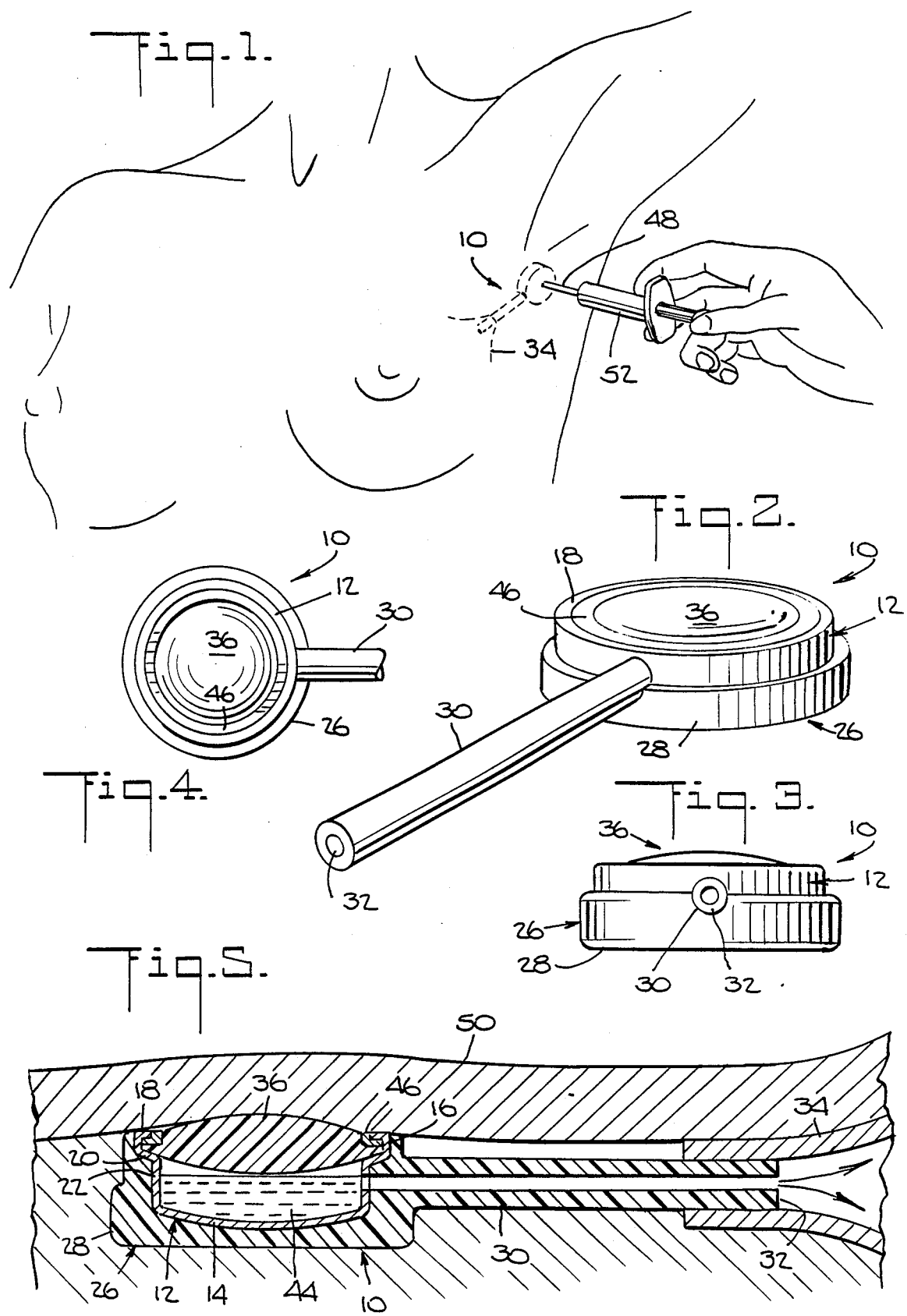

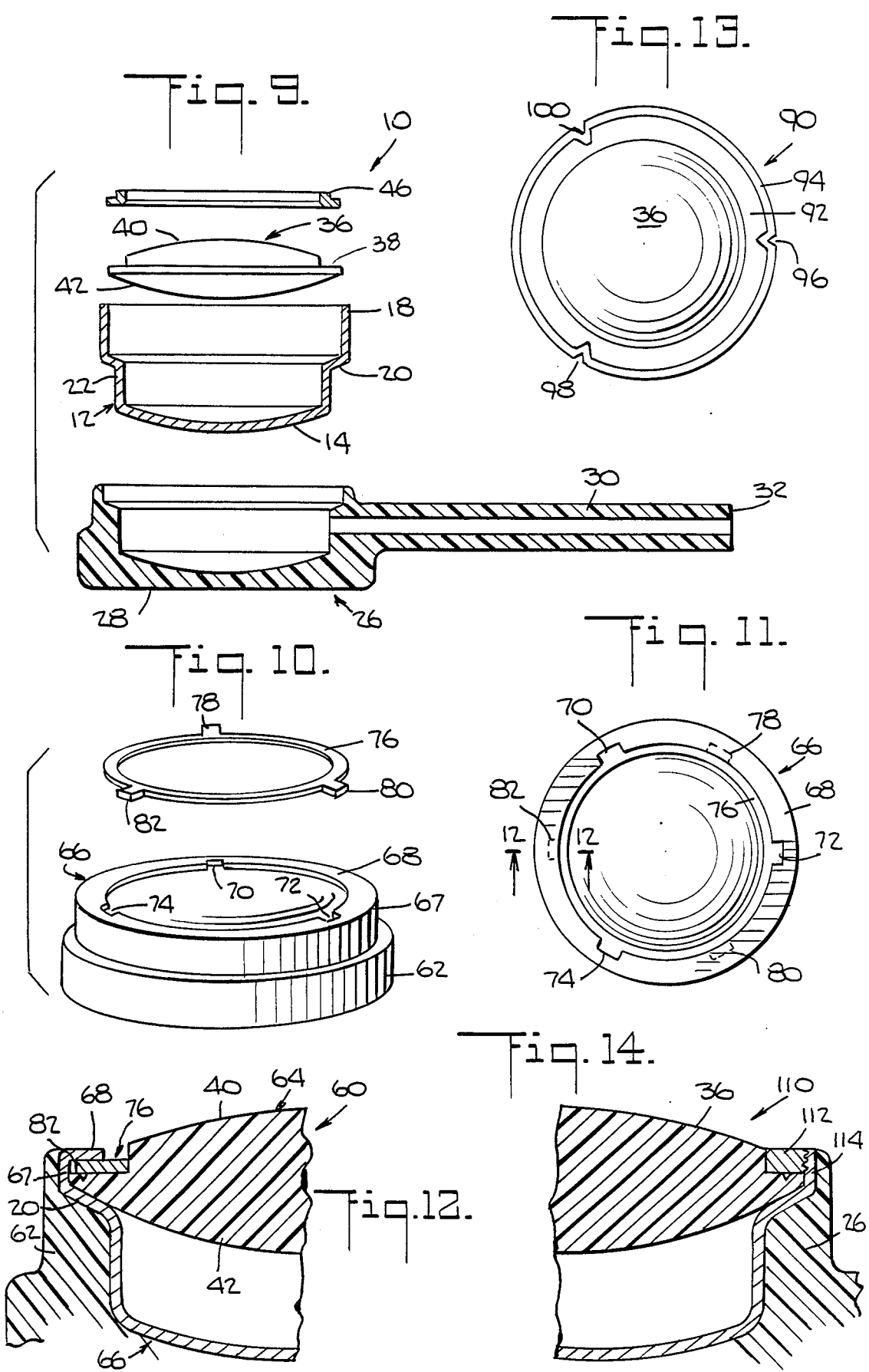

SELF SEALING SUBCUTANEOUS INFUSION AND WITHDRAWAL DEVICE

BACKGROUND OF THE INVENTION

This invention relates to devices for injecting or withdrawing fluid at predetermined regions of the body, and more particularly to a novel self-sealing subcutaneous infusion and withdrawal device.

Prosthetic devices are often implanted in the body to restore shapes and contours that have been surgically altered or accidentally deformed. Many prostheses maintain their desired shape or contour by absorbing or storing fluid that is specially introduced into the prosthesis from an external source. In addition it is often necessary to periodically vary the volume of fluid within the prosthesis to restore proper pocket tension or to modify the shape or contour of the prosthesis.

Rather than inject fluid directly into a prosthesis it has been found beneficial to infuse the fluid into a fluid transfer or dispensing device such as a septum which directs the fluid to its intended site. Preferably the septum is also implanted in the body to facilitate fluid replacement with minimum discomfort to the recipient.

One known device for administering fluid to a patient as disclosed in U.S. Pat. No. 4,543,088, comprises an elastomeric housing that defines an inner fill chamber. Except for the base, the housing walls can be penetrated on all sides by a needle. Consequently, the needle that enters one side of the housing for filling or withdrawal purposes can pass through another side of the housing, completely bypassing the fill chamber. Since this device is used subcutaneously there is no way of observing whether an injection of fluid is being received in the fill chamber or is bypassing said chamber because the needle has passed through the housing wall.

A transcutaneous device used for dialysis, as shown in U.S. Pat. No. 4,490,137, discloses a rigid metallic reservoir that makes direct contact with the body tissue upon implantation. The disclosed device includes a tube formed of separate individual interconnected sections that can leak at the connection seams. Furthermore, the unyielding structure of the metallic reservoir can cause discomfort upon implantation. The device also includes a needle penetrable surface that is not self sealing. Consequently, upon withdrawal of the needle, a fluid path can be established causing leakage. There is also a possibility of reflux back along the surface of the needle during injection.

It is thus desirable to provide a subcutaneous self-sealing infusing and withdrawal device that can be comfortably implanted, is not subject to leakage and minimizes the possibility of a needle passing into and out of the fluid chamber.

OBJECTS AND SUMMARY OF THE INVENTION

Among the several objects of the invention may be noted the provision of a novel self-sealing subcutaneous infusion and withdrawal device, a novel infusion and withdrawal device having a leak-tight mechanical seal, a novel infusion and withdrawal device having enhanced sealing capabilities, a novel infusion and withdrawal device having a seal with oppositely formed convex surfaces which provide a compression load around the surface of a needle during injection to resist reflux back along the surface of the needle, a novel infusion and withdrawal device wherein the seal is fabric reinforced, a novel infusion and withdrawal device which minimizes the bypassing of a fill chamber by a needle, a novel infusion and withdrawal device wherein the needle stop has a spherical bottom, a novel infusion and withdrawal device that includes a jacket, and wherein a fluid transfer tube is an integral part of the jacket, and a novel method of making an infusion and withdrawal device.

Other objects and features of the invention will be in part apparent and in part pointed out hereinafter.

In accordance with the present invention, the self-sealing subcutaneous infusion and withdrawal device includes a needle stop member that defines a fluid chamber. The needle stop member is enveloped by a jacket which includes an integrally formed fluid transfer tube. The fluid transfer tube is aligned with an opening in the needle stop member.

The needle stop member has a spherical base portion and a mouth portion that is sealed by a needle-penetrable seal member that is preferably fabric reinforced. The seal member has opposite convex surfaces one of which extends into the fluid chamber, the other of which extends outside the fluid chamber.

A clamping member cooperates with the mouth portion of the needle stop member to clamp the seal member against the needle stop member to provide a leak-tight seal between the seal member and the needle stop member. For example, in one embodiment of the invention, the mouth portion of the needle stop is rolled over the clamping ring to press the seal member against the needle stop. In another embodiment of the invention, the clamping member is threaded to the mouth portion of the needle stop. The threading of the clamping ring squeezes the seal member against the needle stop member to provide a leak-tight seal.

In another embodiment of the invention, the clamping member and the mouth portion of the needle stop engage each other in a bayonet joint fashion. In a further embodiment of the invention, the clamping ring and the mouth portion of the needle stop are staked together to fix the position of the clamping ring against the seal member thereby squeezing the seal member against the needle stop member to provide a leak-tight seal. In still another embodiment of the invention the clamping ring is press-fit inside the mouth portion of the needle stop member.

The convex surfaces of the seal member function to provide a compression load around the surface of a needle during injection or withdrawal of fluid from the fluid chamber.

In all embodiments of the invention, the seal member functions as a gasket to provide a leak-tight seal between the clamping member and the needle stop member.

The invention accordingly comprises the constructions and method hereinafter described, the scope of the invention being indicated in the claims.

DESCRIPTION OF THE DRAWINGS

In the accompanying drawings, in which several embodiments of the invention are illustrated, FIG. 1 is a simplified schematic view of a self-sealing subcutaneous infusion and withdrawal device incorporating one embodiment of the invention, the device being shown in an implanted position for infusion by a hypodermic needle;

FIG. 2 is a perspective view thereof;

FIG. 3 is a front view thereof;

FIG. 4 is a fragmentary top plan view thereof;

FIG. 5 is an enlarged sectional view thereof in an implanted position;

FIG. 9 is an exploded view thereof;

FIG. 10 shows the clamping arrangement of another embodiment thereof, with the clamping pieces in separate condition;

FIG. 11 shows the clamping pieces of FIG. 10 in assembled condition;

FIG. 12 is an enlarged fragmentary sectional view taken on the line 12—12 of FIG. 11;

FIG. 13 shows the clamping arrangement of a further embodiment thereof; and

FIG. 14 is an enlarged fragmentary sectional view of a further embodiment thereof.

Corresponding reference characters indicate corresponding parts throughout the several views of the drawings.

DETAILED DESCRIPTION OF THE INVENTION

Figure 6:
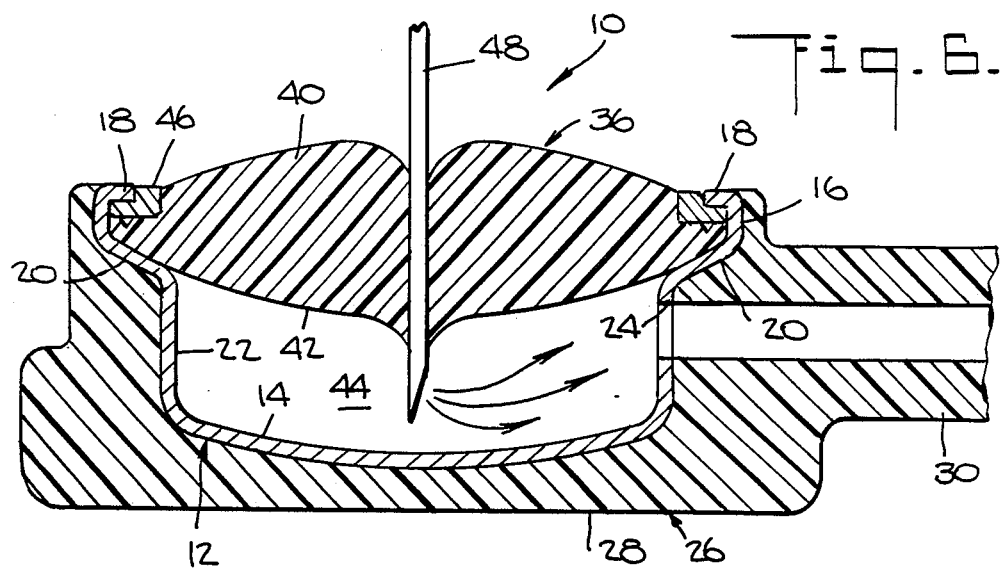
FIG. 6 is an enlarged fragmentary sectional view thereof showing delivery of fluid into the device.

A self-sealing subcutaneous infusion and withdrawal device or septum incorporating one embodiment of the invention is generally indicated by the reference number 10.

The device 10 comprises a generally cup-shaped needle stop member 12 having a base 14 with a spherical contour. The needle stop member 12, which can be formed of stainless steel, has a mouth portion defined by a peripheral channel 16 that includes opposite flanges 18 and 20. The flanges 18 and 20 are extensions of a wall portion 22 of the needle stop member 12. A fluid transfer opening 24 is provided in the wall portion 22.

The needle stop member 12 is enveloped by a jacket member 26, preferably formed of a silicone elastomer. A jacket shell 28 of the jacket member 26 can be molded around the wall portion 22 of the needle stop member 12 to provide a leak-tight bond therebetween. Alternatively, the needle stop member 26 can be disposed in leak-tight relationship into a preformed jacket shell 28 of the jacket member 26, such as shown in FIG. 9.

The leak-tight engagement between a preformed jacket member 26 and the needle stop member 12 can be accomplished for example, by using a suitable known adhesive to bond the needle stop member 12 in the jacket shell 28.

A fluid transfer tube 30 extends from the jacket shell 28 in alignment with the fluid transfer opening 24 of the needle stop member 12. The tube 30 is integrally molded with the jacket shell 28 to avoid any connection seams which are a possible source of leakage. A terminal end 32 of the tube 30 communicates with a fluid receiving site in the body such as a prosthetic device 34.

A needle penetrable seal member 36, preferably formed of a silicone elastomer with prestressed fabric reinforcements, includes a reduced peripheral edge portion 38 that extends into the channel 16 of the needle stop member 12. The seal member 36 is formed with opposite convex surfaces 40 and 42. The convex surface 42 extends into a fill chamber 44 defined by the needle stop member 12. The convex surface 40 extends away from the needle stop member 12.

Figure 7:
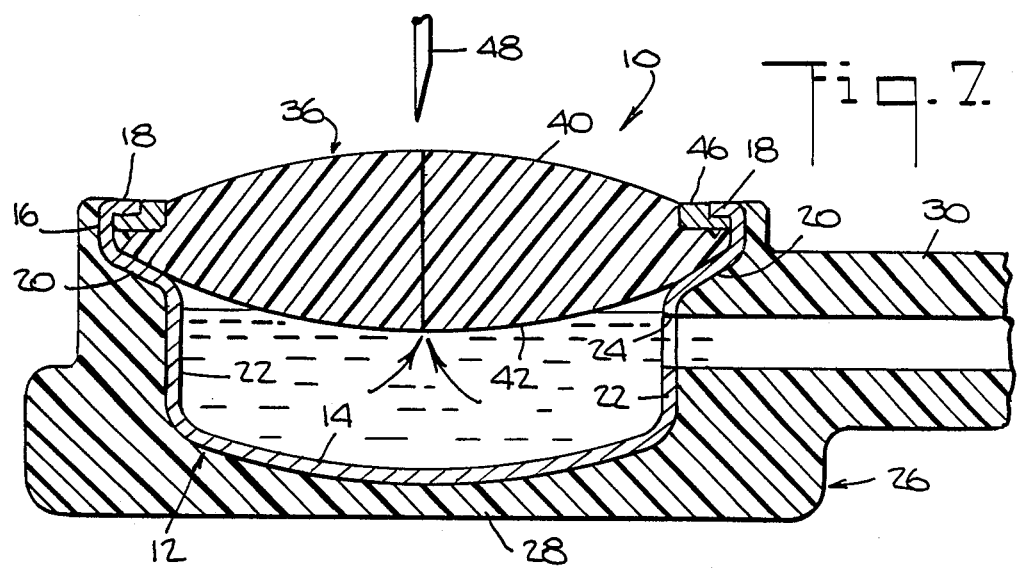
FIG. 7 is a view similar to FIG. 6 showing the needle withdrawn.
Figure 8:
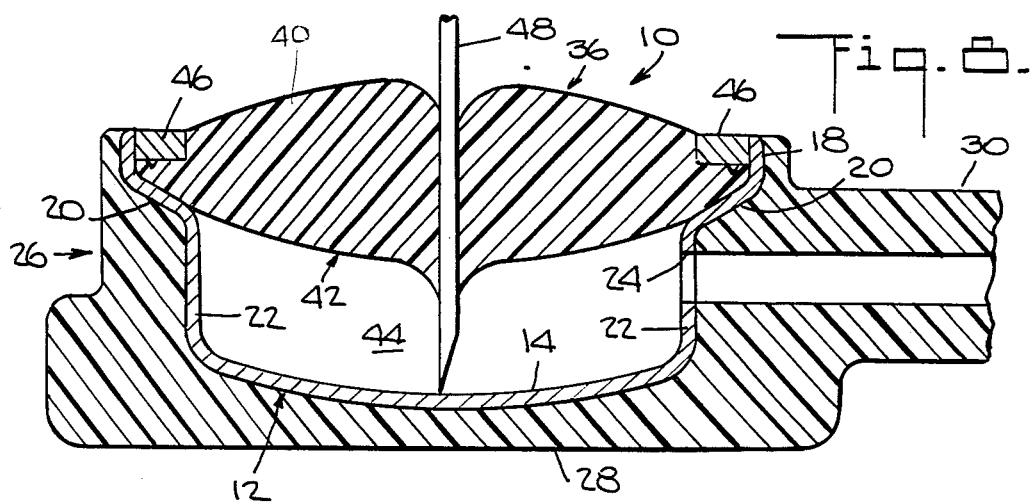
FIG. 8 is a view similar to FIG. 6 showing the needle at its bottom limit position.

The seal member 36 is locked in the channel 16 of the needle stop member 12 by locking means that include a clamping ring member 46 which can be formed of stainless steel. Referring to FIG. 9, the seal locking arrangement is accomplished by disposing the seal member 36 onto the flange 20 of the needle stop member 12. The clamping ring member 46 is then positioned onto the reduced peripheral edge portion 38 of the seal member 36. The wall extension 18 of the needle stop member 12 is rolled over onto the clamping ring 46 in any suitable known manner to form the flange 18 which is oriented as shown in FIGS. 6-8, for example. The rolled-over flange 18 forces the clamping ring 46 against the reduced peripheral edge portion 38 of the seal member 36. The reduced peripheral edge portion 38 is thus squeezed against the flange 20 of the needle stop member 12 to provide a mechanical leak-tight seal between the seal member 36 and the needle stop member 12. The reduced peripheral edge portion 38 of the seal member 36 thus functions as a sealing gasket.

The dimensional relationship between the clamping ring 46 and the reduced peripheral edge portion 38 of the seal member 36 is selected such that the seating of the clamping ring 46 on the reduced peripheral edge portion 38 in the needle stop member 12 causes a considerable compression load to be placed on the seal member 36, especially at the convex surfaces 40 and 42. As a result of this compression load, the seal member 36 seals tightly around the surface of a needle 48 during injection or withdrawal of fluid from the fill chamber 44.

The enhanced sealing capability of the seal member 36 permits use of larger filling needles than are generally customary, thereby facilitating the fluid infusion and fluid withdrawal processes.

If desired the clamping ring 46 can be press-fit in the needle stop member 12 at the peripheral flange 18 (FIG. 9). The interference fit between the clamping ring 46 and the needle stop member 12 locks the clamping ring 46 against the seal member 36 and thus provides the desired sealing force between the seal member 36 and the needle stop member 12. Under this arrangement there would be no need to roll over the flange 18 onto the clamping ring 46. Thus the roll over portion of the flange 18 can be eliminated as shown in FIG. 8.

In using the device 10, an implantation thereof is made under the skin 50 with the tube 30 directed toward a prosthesis 34, for example. Before the fill chamber 44 can be infused, the device 10 is located by palpating the covering skin 50 in the area of the device 10.

A syringe 52 containing the desired fluid is directed toward the device 10 to permit the needle 48 to penetrate the seal member 36. As shown in FIG. 6, the seal member 36, upon penetration by the needle 48, seals tightly around the surface of the needle 48 during injection without deflecting into the fill chamber 44. The stability of the seal member 36 in withstanding deflection, despite the penetrating force of the needle 48, is due to a compression load imposed on the seal member 36 by the clamping ring 46 and the convex surfaces 40 and 42 of the seal member 36.

It should be noted that the seal member 36 does not include a gel fill, which has a tendency to occlude the filling needle 48. A seal member that has a gel fill can be cored out by a needle, and the cored pieces are likely to obstruct or block the flow of fluid to a prosthesis. Furthermore, the coring out of portions of a seal member will permit a reflux of fluid back along the surface of a needle. In addition, when the needle is withdrawn after a piece of sealing member has been cored away by the needle, a fluid path can be established through the seal member causing leakage.

The present seal member 36, by virtue of a silicone elastomer construction that is reinforced with prestressed fabric, without any gel fill, minimizes the possibility of coring of the seal member during penetration of the needle 48.

The cup-shaped structure of the needle stop member 12 helps prevent the needle 48 from passing out of the fill chamber 44 after it has passed through the seal member 36. The cup-shaped structure also acts to prevent the jacket member 26 from peeling away from the needle stop member when the device 10 becomes pressurized.

The fluid injected into the fill chamber 44 by the needle 48 becomes pressurized and, as shown in FIG. 6, passes through the fluid transfer tube 30 for passage to the prosthesis 34. Should the needle 48 reach the base 14 of the needle stop member 12, as shown in FIG. 8, it will be prevented from passing outside the fill chamber 44 due to the metallic puncture-resistant structure of the needle stop member 12.

When the needle 48 is withdrawn from the seal member 36, as shown in FIG. 7, the compression forces on the seal member 36 imposed by the clamping ring 46 tightly seal the opening made by the withdrawn needle 48 thereby resisting leakage through the seal member 36.

The precise dimensions of the device 10 may vary since they are based upon the implant location and the dimensional characteristics of the prosthesis. Nevertheless, to exemplify the magnitudes being dealt with, the seal member 36 can have an outer diameter of approximately 0.995 inches and a diameter at the reduced peripheral edge portion of approximately 0.730 inches. The convex surfaces 40 and 42 can have spherical radii of 1.031 inches and the reduced peripheral edge portion 38 can have a minimum thickness of 0.031 inches. The clamping ring member 46 can have an outside diameter of approximately 1.000 inches and an inside diameter of approximately 0.750 inches. An intermediate diameter of the clamping ring 46 between the inside and outside diameters can be approximately 0.875 inches. The needle stop member fill chamber can have a diameter of approximately 0.750 inches and the spherical radius of the base can be approximately 1.190 inches. The fluid transfer opening 24 can have a diameter of approximately 0.060 inches. The inside diameter of the needle stop member 12 at the wall extension 18 as shown in FIG. 9 can be approximately 0.999 inches. The height of the needle stop member 12 up to the flange 20 can be approximately 0.274 inches. The wall thickness of the needle stop member 12 can be approximately 0.020 inches.

Another embodiment of the septum is generally indicated by the reference number 60 in FIG. 12. The device 60 includes a jacket member 62 and a seal member 64 identical to the jacket member 26 and the seal member 36 of the device 10.

A needle stop member 66 differs from the needle stop member 12 of the device 10 at a peripheral channel 67 having a bayonet-type flange 68 with three bayonet slots 70, 72 and 74. A bayonet-type clamping ring 76 includes projections 78, 80 and 82 that engage in the slots 70, 72 and 74.

The needle stop member 66 is jacketed by the jacket member 26 in a manner similar to that described for the device 10.

Sealing of the device 60 is accomplished by positioning the seal member 64 on the flange 20 of the peripheral channel 67. The clamping ring projections 78, 80 and 82 are then aligned with the slots 70, 72 and 74 of the flange 68 to permit entry of the ring 76 into the channel 67. The ring 76 is rotated to move the projections 78, 80 and 82 past the slots 70, 72 and 74 as shown in FIG. 11.

The clamping ring 76 and the reduced peripheral edge portion 38 of the seal member 64 exceeds the width of the space between the flanges 68 and 20 of the peripheral channel 67. The clamping ring 76 thus squeezes the reduced peripheral edge portion 38 of the seal member 64 against the flange 20 to provide a leak-tight seal between the seal member 64 and the needle stop member 66. The device 60 is used in a manner similar to that described for the device 10.

Another embodiment of the invention includes a clamping arrangement generally indicated by the reference number 90 in FIG. 13.

Other parts of the septum that incorporate the clamping arrangement 90 have been omitted for the sake of clarity since they are identical to the structure that has been previously described. The clamping arrangement 90 includes a clamping ring 92 that is staked to a needle stop member 94 at staking points 96, 98 and 100. The needle stop member 94 is analogous to the needle stop member 12 but does not include the flange 18. Thus the clamping ring 92 is staked to the needle stop member 94 at a predetermined position wherein the clamping ring 92 exerts a force on the seal member 36 similar to that provided by the clamping ring 46 of the device 10.

In a further embodiment of the invention generally indicated by the reference number 110 in FIG. 14, a clamping ring 112 is threaded to a needle stop member 114 to provide the desired sealing force between the seal member 36 and the needle stop member 114.

The device 110 is otherwise equivalent to the device 10 and is used in a manner similar to that previously described for the device 10.

Some advantages of the present invention evident from the foregoing description include a septum that provides an enhanced seal around an injection needle because of increased compressive forces imposed on a seal member. A further advantage is that the septum includes a needle stop member that substantially surrounds all access points of a needle thereby minimizing the likelihood that the needle will pass into and out of the fill chamber of the septum. Still another advantage of the septum is that the seal member is provided with convex surfaces and the bottom of the needle stop member includes a spherical surface. Further advantages of the septum include a one-piece jacketing arrangement having an integral fluid transfer tube that eliminates any seams or connection points. A further advantage is that the seal member is sealed against the needle stop member by a mechanical sealing arrangement. Furthermore, the jacketing of the needle stop member assures relatively comfortable implantation of the septum.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A self-sealing subcutaneous infusion and withdrawal device comprising, a cup-shaped needle stop member having a wall portion defining a mouth, and a base opposite said mouth, a fluid transfer opening formed in said wall portion, a jacket member enveloping said needle stop member, said jacket member including a fluid transfer tube aligned with the fluid transfer opening of said needle stop member, a needle penetrable seal member for sealing the mouth of said needle stop member, said seal member having opposite convex surfaces, one of said convex surfaces extending into said needle stop member and the other of said convex surfaces extending away from said needle stop member, said other surface having a peripheral ledge, and clamping means for clamping said peripheral ledge of said seal member to the mouth of said needle stop member.

2. The device as claimed in claim 1, wherein the base of said needle stop member has a spherical contour.

3. The device as claimed in claim 1, wherein said jacket member and said fluid transfer tube are formed in one piece.

4. The device as claimed in claim 1, where said clamping means include a clamping member and a peripheral channel is formed at the mouth of said needle stop member for accommodating said clamping member and the periphery of said seal member such that said clamping member urges said seal member against said channel to provide a leak-tight seal at the mouth of said needle stop member.

5. The device as claimed in claim 1, wherein said clamping means include a clamping member and means for holding said clamping member against said seal member to provide a leak-tight seal between said seal member and said needle stop member, and to provide a predetermined compression load on the seal member that enhances the sealing capability of the seal member around an injection needle.

6. A self-sealing subcutaneous infusion and withdrawal device comprising:
   (a) a cup-shaped needle stop member defining a fluid chamber with a fluid transfer opening, said needle stop member including a mouth portion;
   (b) jacket means enveloping said needle stop member; and
   (c) needle penetrable sealing means for sealing said fluid chamber such that said fluid chamber may be accessed by a needle penetrating said sealing means, said sealing means including a seal member having two opposing convex surfaces, one of said surfaces extending outside said fluid chamber and having a peripheral ledge, said other convex surface extending inside said fluid chamber, said sealing means further including a clamping member for clamping said peripheral ledge of said seal member against said needle stop member to seal said fluid chamber.

7. The device as claimed in claim 6 wherein said jacket member includes a fluid transfer tube aligned with said fluid transfer opening.

8. The device as claimed in claim 6, wherein said needle stop member includes a base having a spherical contour that is substantially concave within the fluid chamber.

9. The device as claimed in claim 7, wherein said seal member is fabric reinforced.

10. The device as claimed in claim 9, wherein said fabric is prestressed.

11. The device as claimed in claim 6, including means for fixing the position of said clamping member against said seal member to provide a leak-tight seal between said seal member and said needle stop member, and to provide a predetermined compression load on the seal member that enhances the sealing capability of the seal member around an injection needle.

12. The device as claimed in claim 11, wherein said fixing means include deforming said needle stop member around said clamping member to fix said clamping member in position against said seal member.

13. The device as claimed in claim 11, wherein said fixing means includes threading said clamping member to said needle stop member to fix said clamping member in position against said seal member.

14. The device as claimed in claim 11, wherein said fixing means include staking said needle stop member to said clamping member to fix said clamping member in position against said seal member.

15. The device as claimed in claim 11, wherein said needle stop member has a top edge and said fixing means include rolling said top edge over said clamping member to fix said clamping member in position against said seal member.

16. The device as claimed in claim 11, wherein said fixing means include providing a bayonet mount between said needle stop member and said clamping member to fix said clamping member in position against said seal member.

17. The device as claimed in claim 11, wherein said fixing means include providing an interference fit between said clamping member and said needle stop member to fix said clamping member in position against said seal member.

18. A method of making a self-sealing subcutaneous infusion and withdrawal device:
   (a) forming a needle stop member in the general shape of a cup with a mouth portion and a wall portion, and providing a fluid transfer opening in the wall of the needle stop member,
   (b) providing a flexible jacket around the needle stop member with a fluid transfer tube that aligns with the fluid transfer opening in the needle stop member,
   (c) forming a seal member with two opposing convex surfaces, one of the convex surfaces having a peripheral ledge,
   (d) sealing the mouth of the needle stop with said seal member with the convex surface having a peripheral ledge extending outside the needle stop member, and the other convex surface extending inside the needle stop member,
   (e) clamping said peripheral ledge to the mouth of the needle stop member so as to provide a leak-tight seal between the seal member and the needle stop member and a compression load on the seal member that enhances the sealing capability of the seal member around an injection needle.

* * * * *